(12) United States Patent
Wu et al.

(10) Patent No.: US 11,244,446 B2
(45) Date of Patent: Feb. 8, 2022

(54) SYSTEMS AND METHODS FOR IMAGING

(71) Applicant: SHANGHAI UNITED IMAGING INTELLIGENCE CO., LTD., Shanghai (CN)

(72) Inventors: Ziyan Wu, Cambridge, MA (US); Shanhui Sun, Cambridge, MA (US); Arun Innanje, Cambridge, MA (US)

(73) Assignee: SHANGHAI UNITED IMAGING INTELLIGENCE CO., LTD., Shanghai (CN)

(*) Notice: Subject to any disclaimer, the term of this patent is extended or adjusted under 35 U.S.C. 154(b) by 172 days.

(21) Appl. No.: 16/664,690

(22) Filed: Oct. 25, 2019

(65) Prior Publication Data

US 2021/0125330 A1 Apr. 29, 2021

(51) Int. Cl.
*G06T 7/00* (2017.01)
*G06N 3/08* (2006.01)

(52) U.S. Cl.
CPC .......... *G06T 7/0012* (2013.01); *G06N 3/084* (2013.01); *G06T 2207/10072* (2013.01); *G06T 2207/20081* (2013.01); *G06T 2207/20084* (2013.01); *G06T 2207/30004* (2013.01)

(58) Field of Classification Search
CPC combination set(s) only.
See application file for complete search history.

(56) References Cited

U.S. PATENT DOCUMENTS

| | | | |
|---|---|---|---|
| 7,254,623 B1* | 8/2007 | Toth | A61B 6/032 707/999.005 |
| 10,359,271 B2* | 7/2019 | Rempel | G01N 21/01 |
| 2005/0147303 A1* | 7/2005 | Zhou | G06K 9/6206 382/190 |
| 2012/0098838 A1* | 4/2012 | Lehmann | G06T 19/00 345/501 |
| 2012/0232853 A1* | 9/2012 | Voigt | G06T 7/344 703/1 |
| 2013/0198687 A1* | 8/2013 | Bird | A61B 5/7435 715/810 |
| 2017/0116748 A1* | 4/2017 | Scutaru | G06K 9/6256 |
| 2017/0147782 A1 | 5/2017 | Haberland et al. | |
| 2018/0348998 A1* | 12/2018 | Mueller | G06N 5/022 |
| 2019/0122361 A1* | 4/2019 | Lilliestr Le | A61B 34/10 |
| 2019/0332619 A1* | 10/2019 | De Sousa Webber | G06F 40/30 |

OTHER PUBLICATIONS

Siemens Healthcare GmbH, Get Two Steps ahead with Dual Source CT-SOMATOM Force, 2018, 68 pages.

* cited by examiner

*Primary Examiner* — Tsung Yin Tsai
(74) *Attorney, Agent, or Firm* — Metis IP LLC

(57) ABSTRACT

The present disclosure relates to systems and methods for imaging. The method may include obtaining a real-time representation of a subject. The method may also include determining at least one scanning parameter associated with the subject by automatically processing the representation according to a parameter obtaining model. The method may further include performing a scan on the subject based at least in part on the at least one scanning parameter.

20 Claims, 9 Drawing Sheets

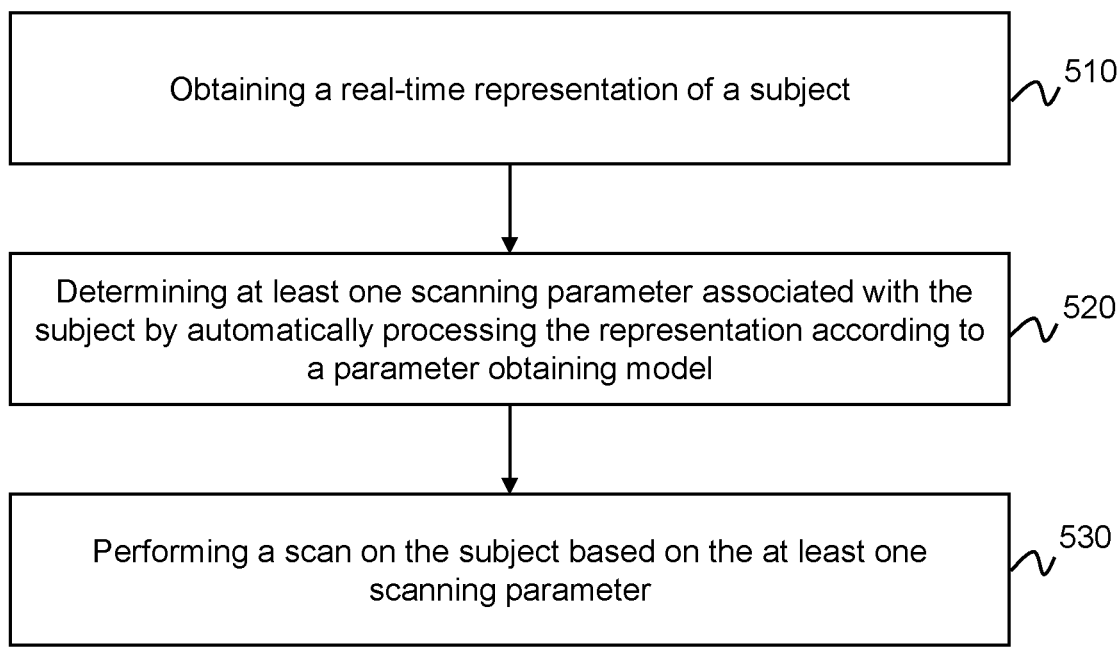
FIG. 5-A

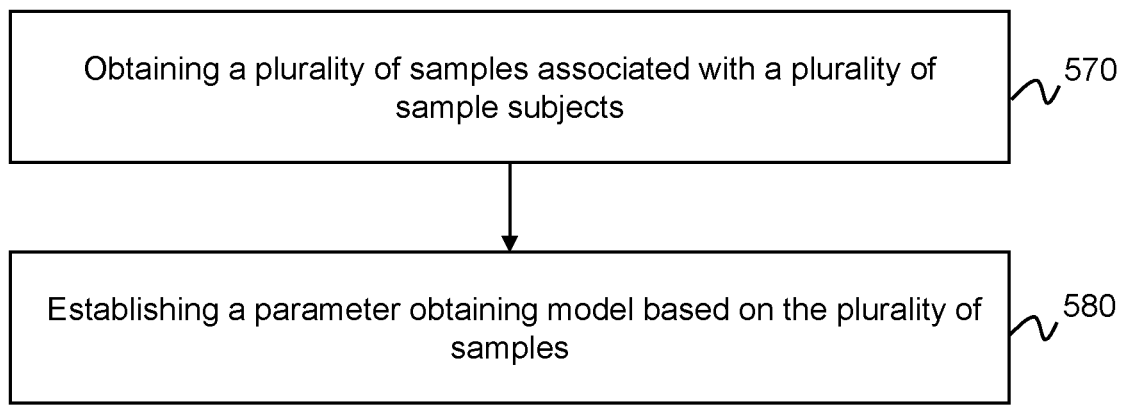
FIG. 5-B

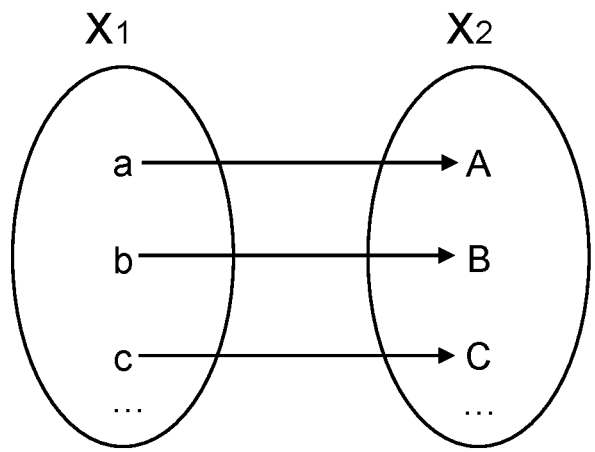
FIG. 6-A
| Representation | Scanning parameter group |
|---|---|
| a | A |
| b | B |
| c | C |
| ... | ... |
FIG. 6-B

SYSTEMS AND METHODS FOR IMAGING

TECHNICAL FIELD

The present disclosure generally relates to the medical field, and in particular, to systems and methods for medical imaging.

BACKGROUND

With the development of medical science and technology, medical imaging becomes more and more important. A medical imaging system (e.g., a magnetic resonance (MR) imaging system, a computed tomography (CT) imaging system, an X-ray imaging system) can perform scanning on a subject based on scanning parameters and determine medical images based on scanning results. In current practice, scanning parameters are usually set manually by doctors or technicians who operate the scanning, which may reduce imaging efficiency. Therefore, it is desirable to provide systems and methods for automatically determining scanning parameters, thereby improving imaging efficiency.

SUMMARY

An aspect of the present disclosure relates to a system for imaging. The system may include at least one storage medium including a set of instructions and at least one processor in communication with the at least one storage medium. When executing the set of instructions, the at least one processor may be directed to cause the system to perform operations. The operations may include obtaining a real-time representation of a subject. The operations may also include determining at least one scanning parameter associated with the subject by automatically processing the representation according to a parameter obtaining model. The operations may further include performing a scan on the subject based at least in part on the at least one scanning parameter.

In some embodiments, the representation of the subject may include a real-time image of the subject, a model indicating a real-time posture of the subject, and/or an internal anatomical representation of the subject.

In some embodiments, the at least one scanning parameter may include a scanning range, a scanning dose, a scanning path, a scanning distance, a scanning angle, and/or a scanning sequence.

In some embodiments, the parameter obtaining model may be pre-established based on a plurality of samples associated with a plurality of sample subjects. Each of the plurality of samples may include a sample representation of a sample subject and a sample scanning parameter group including at least one sample scanning parameter associated with the sample subject.

In some embodiments, each of the plurality of samples may be obtained by performing a scan on a sample subject and/or a simulation approach.

In some embodiments, the parameter obtaining model may include a machine learning model trained based on the plurality of samples.

In some embodiments, the parameter obtaining model may include a library including a plurality of mappings. Each mapping may be between a sample representation and a sample scanning parameter group.

In some embodiments, the determining at least one scanning parameter associated with the subject by automatically processing the representation according to a parameter obtaining model may include identifying, from the library, a target sample representation based on a degree of similarity between the target sample representation and the representation of the subject; and determining the at least one scanning parameter associated with the subject based on at least one sample scanning parameter included in a sample scanning parameter group corresponding to the target sample representation.

In some embodiments, the identifying, from the library, the target sample representation based on the degree of similarity between the target sample representation and the representation of the subject may include for each of at least some of the plurality of mappings, determining a degree of similarity between a sample representation of the mapping and the representation of the subject; and identifying, based on the determined degrees of similarities, a sample representation corresponding to a mapping of the at least some mappings as the target sample representation.

In some embodiments, the degree of similarity between a sample representation of the mapping and the representation of the subject may be determined based on a machine learning model.

In some embodiments, the identifying, based on the determined degrees of similarities, the sample representation corresponding to the mapping of the at least some mappings as the target sample representation may include designating a sample representation corresponding to a mapping of the at least some mappings whose degree of similarity with the representation of the subject is higher than a threshold as the target sample representation.

In some embodiments, the determining the at least one scanning parameter associated with the subject based on the at least one sample scanning parameter included in the sample scanning parameter group corresponding to the target sample representation may include designating the at least one sample scanning parameter included in the sample scanning parameter group corresponding to the target sample representation as the at least one scanning parameter associated with the subject.

In some embodiments, the determining the at least one scanning parameter associated with the subject based on the at least one sample scanning parameter included in the sample scanning parameter group corresponding to the target sample representation may include determining the at least one scanning parameter associated with the subject by modifying the at least one sample scanning parameter included in the sample scanning parameter group corresponding to the target sample representation.

In some embodiments, the determining the at least one scanning parameter associated with the subject based on the at least one sample scanning parameter included in the sample scanning parameter group corresponding to the target sample representation may include identifying, from the library, a second target sample representation based on a second degree of similarity between the second target sample representation and the representation of the subject; and determining the at least one scanning parameter associated with the subject based on at least one sample scanning parameter included in a sample scanning parameter group corresponding to the second target sample representation.

In some embodiments, the at least one processor may be directed to cause the system to perform the operations further including transmitting the at least one scanning parameter associated with the subject to a user; receiving from the user an instruction regarding the at least one scanning parameter associated with the subject; and performing the scan on the subject based at least in part on the at least one scanning parameter and the instruction from the user.

In some embodiments, the instruction may include an approval to designate the at least one scanning parameter associated with the subject as a scanning parameter for the scanning, a modification of at least a portion of the at least one scanning parameter associated with the subject, a rejection of at least a portion of the at least one scanning parameter associated with the subject, and/or a supplement to the at least one scanning parameter associated with the subject.

In some embodiments, the at least one processor may be directed to cause the system to perform the operations further including modifying at least a portion of the at least one scanning parameter associated with the subject based on the instruction.

In some embodiments, the at least one processor may be directed to cause the system to perform the operations further including performing the scan on the subject based at least in part on the modified at least one scanning parameter associated with the subject.

In some embodiments, the at least one processor may be directed to cause the system to perform the operations further including supplementing at least one additional scanning parameter to the at least one scanning parameter associated with the subject based on the instruction.

In some embodiments, the at least one processor may be directed to cause the system to perform the operations further including performing the scan on the subject based at least in part on the supplemented scanning parameter associated with the subject including the at least one additional scanning parameter.

Another aspect of the present disclosure relates to a method for imaging. The method may include obtaining a real-time representation of a subject. The method may also include determining at least one scanning parameter associated with the subject by automatically processing the representation according to a parameter obtaining model. The method may further include performing a scan on the subject based at least in part on the at least one scanning parameter.

In some embodiments, the representation of the subject may include a real-time image of the subject, a model indicating a real-time posture of the subject, and/or an internal anatomical representation of the subject.

In some embodiments, the at least one scanning parameter may include a scanning range, a scanning dose, a scanning path, a scanning distance, a scanning angle, and/or a scanning sequence.

In some embodiments, the parameter obtaining model may be pre-established based on a plurality of samples associated with a plurality of sample subjects. Each of the plurality of samples may include a sample representation of a sample subject and a sample scanning parameter group including at least one sample scanning parameter associated with the sample subject.

In some embodiments, each of the plurality of samples may be obtained by performing a scan on a sample subject and/or a simulation approach.

In some embodiments, the parameter obtaining model may include a machine learning model trained based on the plurality of samples.

In some embodiments, the parameter obtaining model may include a library including a plurality of mappings. Each mapping may be between a sample representation and a sample scanning parameter group.

In some embodiments, the determining the at least one scanning parameter associated with the subject by automatically processing the representation according to the parameter obtaining model may include identifying, from the library, a target sample representation based on a degree of similarity between the target sample representation and the representation of the subject; and determining the at least one scanning parameter associated with the subject based on at least one sample scanning parameter included in a sample scanning parameter group corresponding to the target sample representation.

In some embodiments, the identifying, from the library, the target sample representation based on the degree of similarity between the target sample representation and the representation of the subject may include for each of at least some of the plurality of mappings, determining a degree of similarity between a sample representation of the mapping and the representation of the subject; and identifying, based on the determined degrees of similarities, a sample representation corresponding to a mapping of the at least some mappings as the target sample representation.

In some embodiments, the degree of similarity between a sample representation of the mapping and the representation of the subject may be determined based on a machine learning model.

In some embodiments, the identifying, based on the determined degrees of similarities, the sample representation corresponding to the mapping of the at least some mappings as the target sample representation may include designating a sample representation corresponding to a mapping of the at least some mappings whose degree of similarity with the representation of the subject is higher than a threshold as the target sample representation.

In some embodiments, the determining the at least one scanning parameter associated with the subject based on the at least one sample scanning parameter included in the sample scanning parameter group corresponding to the target sample representation may include designating the at least one sample scanning parameter included in the sample scanning parameter group corresponding to the target sample representation as the at least one scanning parameter associated with the subject.

In some embodiments, the determining the at least one scanning parameter associated with the subject based on the at least one sample scanning parameter included in the sample scanning parameter group corresponding to the target sample representation may include determining the at least one scanning parameter associated with the subject by modifying the at least one sample scanning parameter included in the sample scanning parameter group corresponding to the target sample representation.

In some embodiments, the determining the at least one scanning parameter associated with the subject based on the at least one sample scanning parameter included in the sample scanning parameter group corresponding to the target sample representation may include identifying, from the library, a second target sample representation based on a second degree of similarity between the second target sample representation and the representation of the subject; and determining the at least one scanning parameter associated with the subject based on at least one sample scanning parameter included in a sample scanning parameter group corresponding to the second target sample representation.

In some embodiments, the method may further include transmitting the at least one scanning parameter associated with the subject to a user; receiving from the user an instruction regarding the at least one scanning parameter associated with the subject; and performing the scan on the subject based at least in part on the at least one scanning parameter and the instruction from the user.

In some embodiments, the instruction may include an approval to designate the at least one scanning parameter associated with the subject as scanning parameter for the scanning, a modification of at least a portion of the at least one scanning parameter associated with the subject, a rejection of at least a portion of the at least one scanning parameter associated with the subject, and/or a supplement to the at least one scanning parameter associated with the subject.

In some embodiments, the method may further include modifying at least a portion of the at least one scanning parameter associated with the subject based on the instruction.

In some embodiments, the method may further include performing the scan on the subject based at least in part on the modified at least one scanning parameter associated with the subject.

In some embodiments, the method may further include supplementing at least one additional scanning parameter to the at least one scanning parameter associated with the subject based on the instruction.

In some embodiments, the method may further include performing the scan on the subject based at least in part on the supplemented scanning parameter associated with the subject including the at least one additional scanning parameter.

A further aspect of the present disclosure relates to a non-transitory computer readable medium including executable instructions. When executed by at least one processor, the executable instructions may direct the at least one processor to perform a method. The method may include obtaining a real-time representation of a subject. The method may also include determining at least one scanning parameter associated with the subject by automatically processing the representation according to a parameter obtaining model. The method may further include performing a scan on the subject based at least in part on the at least one scanning parameter.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 5-A is a flowchart illustrating an exemplary process for imaging according to some embodiments of the present disclosure;

FIG. 5-B is a flowchart illustrating an exemplary process for establishing a parameter obtaining model according to some embodiments of the present disclosure;

FIG. 6-A and FIG. 6-B are schematic diagrams illustrating exemplary mappings between sample representations and sample scanning parameter groups according to some embodiments of the present disclosure;

DETAILED DESCRIPTION

Figure 1:
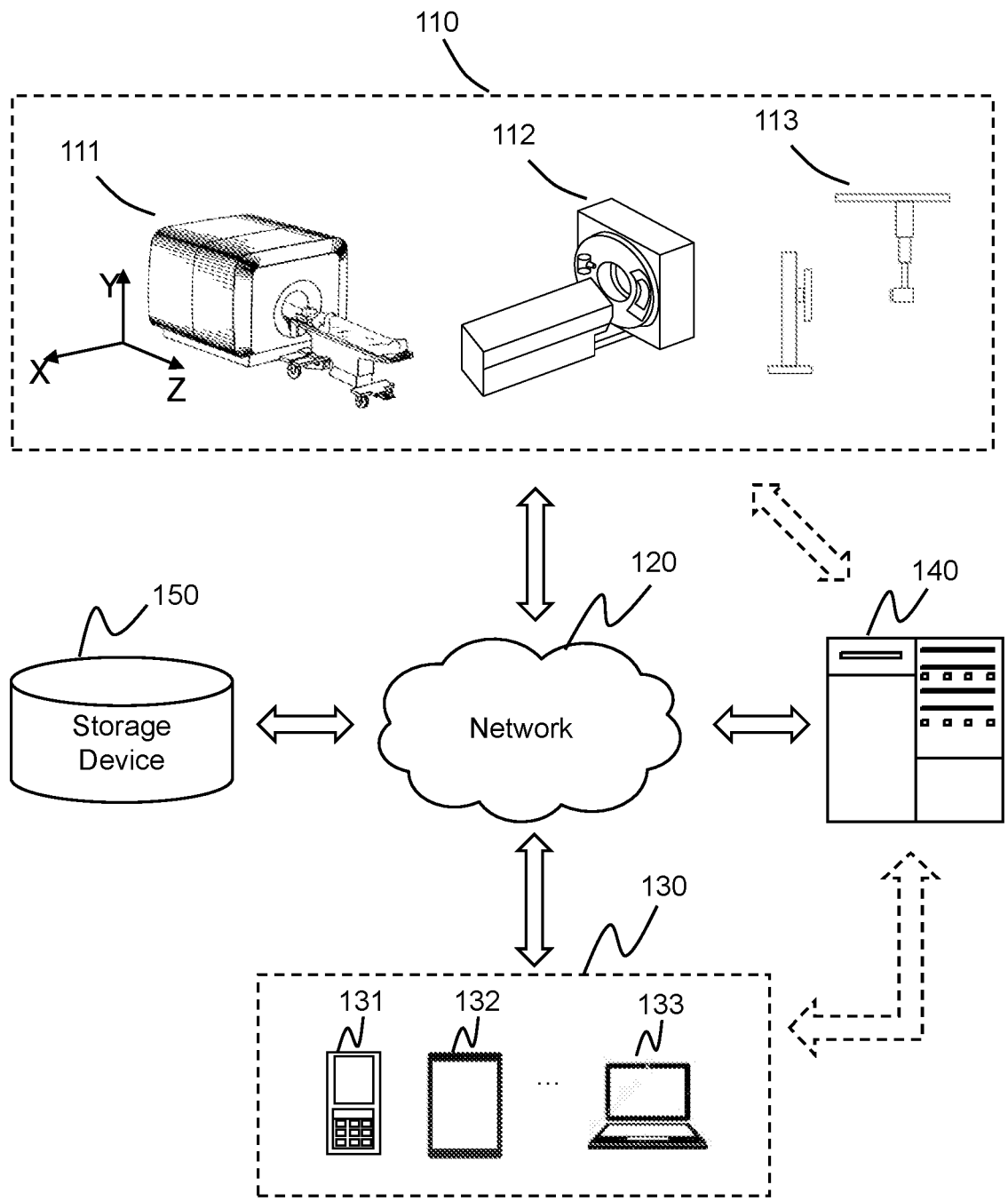
FIG. 1 is a schematic diagram illustrating an exemplary imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this disclosure, specify the presence of stated features, integers, steps, operations, elements, and/or components, but do not preclude the presence or addition of one or more other features, integers, steps, operations, elements, components, and/or groups thereof.

It will be understood that the terms "system," "engine," "unit," "module," and/or "block" used herein are one method to distinguish different components, elements, parts, sections, or assemblies of different levels in ascending order. However, the terms may be displaced by another expression if they achieve the same purpose.

Generally, the words "module," "unit," or "block" used herein refer to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for performing on computing devices (e.g., processor 210 illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to performing). Such software code may be stored, partially or fully, on a storage device of the performing computing device, for performing by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

Provided herein are systems and components for medical imaging and/or medical treatment. In some embodiments, the medical system may include an imaging system. The imaging system may include a single modality imaging system and/or a multi-modality imaging system. The single modality imaging system may include, for example, a magnetic resonance imaging (MRI) system, a positron emission tomography (PET) system, an emission computed tomography (ECT) system, a computed tomography (CT) imaging system, an X-ray imaging system, a molecular imaging (MI) system, a radiation therapy (RT) system, or the like, or any combination thereof. The multi-modality imaging system may include, for example, a computed tomography-magnetic resonance imaging (MRI-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, a computed tomography-positron emission tomography (CT-PET) system, or the like, or any combination thereof. In some embodiments, the medical system may include a treatment system. The treatment system may include a treatment plan system (TPS), image-guided radiotherapy (IGRT), etc. The image-guided radiotherapy (IGRT) may include a treatment device and an imaging device. The treatment device may include a linear accelerator, a cyclotron, a synchrotron, etc., configured to perform a radiotherapy on a subject. The treatment device may include an accelerator of species of particles including, for example, photons, electrons, protons, or heavy ions. The imaging device may include an MRI scanner, a CT scanner (e.g., cone beam computed tomography (CBCT) scanner), a digital radiology (DR) scanner, an electronic portal imaging device (EPID), etc.

An aspect of the present disclosure relates to systems and methods for imaging. The systems may obtain a representation of a subject (e.g., a patient), which may be associated with a real-time image of the subject. The systems may determine at least one scanning parameter associated with the subject by automatically processing the representation according to a parameter obtaining model (e.g., a pre-established library including a plurality of mappings each of which is between a sample representation of a sample subject and a sample scanning parameter group). The systems may further perform a scan on the subject based at least in part on the at least one scanning parameter. According to the systems and methods of the present disclosure, scanning parameters may be automatically determined based on the representation of the subject, which can obviate the need for users (e.g., doctors, imaging technicians) to manually set such scanning parameters, and in turn improve scanning quality, consistency, and imaging efficiency.

FIG. 1 is a schematic diagram illustrating an exemplary imaging system according to some embodiments of the present disclosure. As illustrated, the imaging system 100 may include a scanner 110, a network 120, a terminal device 130, a processing device 140, and a storage device 150. The components of the imaging system 100 may be connected in one or more of various ways. For example, the scanner 110 may be connected to the processing device 140 directly (as indicated by the bi-directional arrow in dotted lines linking the scanner 110 and the processing device 140) or through the network 120. As another example, the storage device 150 may be connected to the processing device 140 directly or through the network 120. As a further example, the terminal device 130 may be connected to the processing device 140 directly (as indicated by the bi-directional arrow in dotted lines linking the terminal device 130 and the processing device 140) or through the network 120.

The scanner 110 may scan an object located within its detection region and generate data relating to the object. In some embodiments, the object may include a patient, a man-made object, etc. In some embodiments, the object may include a specific portion, organ, and/or tissue of a patient.

For example, the object may include a head, a brain, a neck, a body, a shoulder, an arm, a thorax, a cardiac, a stomach, a blood vessel, a soft tissue, a knee, feet, or the like, or any combination thereof. In the present disclosure, "subject" and "object" are used interchangeably. In some embodiments, the scanner 110 may include an MR scanner 111, a CT scanner 112, an X-ray scanner 113, or the like, or any combination thereof.

The MR scanner 111 may include a main magnet assembly for providing a strong uniform main magnetic field to align individual magnetic moments of H atoms within the object. During this process, the H atoms may oscillate around their magnetic poles at their characteristic Larmor frequency. If the object is subjected to an additional magnetic field, which is tuned to the Larmor frequency, the H atoms may absorb additional energy, which rotates the net aligned moment of the H atoms. The additional magnetic field may be provided by an RF excitation signal (e.g., an RF signal generated by RF coils). When the additional magnetic field is removed, the magnetic moments of the H atoms may rotate back into alignment with the main magnetic field thereby emitting MR signals.

The CT scanner 112 may include an X-ray tube that emits ionizing radiation that traverses an examination region and the specific region of the object therein and illuminates a detector array disposed across the examination region and opposite to the X-ray tube. The detector may produce projection data indicative of the detected radiation, which may be reconstructed to generate volumetric image data indicative of the specific region of the object.

The X-ray scanner 113 may include a scanning source that emits X-rays to scan the specific region of the object located on a table. Then a detector may detect one or more X-rays scattered by the specific region of the object, which may be used to generate X-ray images associated with the specific region of the object.

The network 120 may include any suitable network that can facilitate the exchange of information and/or data for the imaging system 100. In some embodiments, one or more components (e.g., the scanner 110, the terminal device 130, the processing device 140, the storage device 150) of the imaging system 100 may communicate with one or more other components of the imaging system 100 via the network 120. For example, the processing device 140 may identify a sample representation based on a degree of similarity between the sample representation and a representation of a subject from a library stored in the storage device 150 via the network 120. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a Zig-Bee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal device 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google™ Glass, an Oculus Rift, a Hololens, a Gear VR, etc. In some embodiments, the scanner 110 and/or the processing device 140 may be remotely operated through the terminal device 130. In some embodiments, the scanner 110 and/or the processing device 140 may be operated through the terminal device 130 via a wireless connection. In some embodiments, the terminal device 130 may receive information and/or instructions inputted by a user, and send the received information and/or instructions to the scanner 110 or the processing device 140 via the network 120. In some embodiments, the terminal device 130 may receive data and/or information from the processing device 140. In some embodiments, the terminal device 130 may be part of the processing device 140. In some embodiments, the terminal device 130 may be omitted.

The processing device 140 may process data and/or information obtained from the scanner 110, the terminal device 130, the storage device 150, and/or any other components associated with the imaging system 100. For example, the processing device 140 may obtain a real-time image from a camera, an optical sensor, or a scanner connected to the imaging system 100 and determine a representation of the subject based on the real-time image. In some embodiments, the processing device 140 may be a single server or a server group. The server group may be centralized or distributed. In some embodiments, the processing device 140 may be local or remote. For example, the processing device 140 may access information and/or data stored in or acquired by the scanner 110, the terminal device 130, the storage device 150, and/or any other components (e.g., a camera, an optical sensor, a measurement device) associated with the imaging system 100 via the network 120. As another example, the processing device 140 may be directly connected to the scanner 110 (as illustrated by the bidirectional arrow in dashed lines connecting the processing device 140 and the scanner 110 in FIG. 1), the terminal device 130 (as illustrated by the bidirectional arrow in dashed lines connecting the processing device 140 and the terminal device 130 in FIG. 1), and/or the storage device 150 to access stored or acquired information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 including one or more components illustrated in FIG. 2 in the present disclosure.

The storage device 150 may store data and/or instructions. In some embodiments, the storage device 150 may store data obtained from the scanner 110, the terminal device 130, and/or the processing device 140. For example, the storage device 150 may store historical scanning information (e.g., historical scanning parameters) associated with a plurality of patients. In some embodiments, the storage device 150 may store data and/or instructions that the processing device 140 may execute or use to perform exemplary methods described in the present disclosure. For example, the storage device 150 may store instructions that the processing device 140 may execute to determine at least one scanning parameter associated with a subject. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components (e.g., the scanner 110, the processing device 140, the terminal device 130) of the imaging system 100. One or more components of the imaging system 100 may access the data or instructions stored in the storage device 150 via the network 120. In some embodiments, the storage device 150 may be directly connected to or communicate with one or more components (e.g., the scanner 110, the processing device 140, the terminal device 130) of the Imaging system 100. In some embodiments, the storage device 150 may be part of the processing device 140.

In some embodiments, the imaging system 100 may further include one or more power supplies (not shown in FIG. 1) connected to one or more components (e.g., the scanner 110, the processing device 140, the terminal device 130, the storage device 150) of the imaging system 100.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 2:
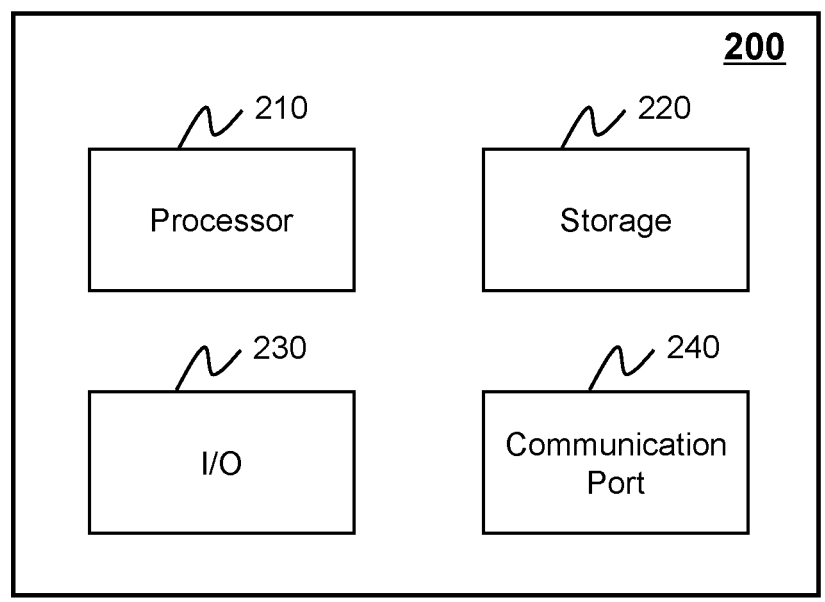
FIG. 2 is a schematic diagram illustrating exemplary hardware and/or software components of an exemplary computing device according to some embodiments of the present disclosure.

FIG. 2 is a schematic diagram illustrating exemplary hardware and/or software components of an exemplary computing device according to some embodiments of the present disclosure. In some embodiments, the processing device 140 may be implemented on the computing device 200. As illustrated in FIG. 2, the computing device 200 may include a processor 210, a storage 220, an input/output (I/O) 230, and a communication port 240.

The processor 210 may execute computer instructions (program code) and perform functions of the processing device 140 in accordance with techniques described herein. The computer instructions may include routines, programs, objects, components, signals, data structures, procedures, modules, and functions, which perform particular functions described herein. For example, the processor 210 may execute the computer instructions to obtain a representation of a subject and determine at least one scanning parameter associated with the subject based on the representation. As another example, the processor 210 may execute the computer instructions to pre-establish a parameter obtaining model and determine the at least one scanning parameter associated with the subject according to the parameter obtaining model. In some embodiments, the processor 210 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 200. However, it should be noted that the computing device 200 in the present disclosure may also include multiple processors, and thus operations of a method that are performed by one processor as described in the present disclosure may also be jointly or separately performed by the multiple processors. For example, if in the present disclosure the processor of the computing device 200 executes both operations A and B, it should be understood that operations A and step B may also be performed by two different processors jointly or separately in the computing device 200 (e.g., a first processor executes operation A and a second processor executes operation B, or the first and second processors jointly execute operations A and B).

The storage 220 may store data/information obtained from the scanner 110, the terminal device 130, the storage device 150, or any other component of the imaging system 100. In some embodiments, the storage 220 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for determining at least one scanning parameter associated with the subject according to a parameter obtaining model.

The I/O 230 may input or output signals, data, or information. In some embodiments, the I/O 230 may enable user interaction with the processing device 140. In some embodiments, the I/O 230 may include an input device and an output device. Exemplary input devices may include a keyboard, a mouse, a touch screen, a microphone, a trackball, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

Merely by way of example, a user (e.g., an operator) may input data related to an object (e.g., a patient) that is being/to be imaged/scanned through the I/O 230. The data related to the object may include identification information (e.g., a name, an age, a gender, a height, a weight, a medical history, contact information, a physical examination result). The user may also input parameters needed for the operation of the scanner 110, such as image contrast and/or ratio, a region of interest (ROI), slice thickness, an imaging type, a scan type, a sampling type, or the like, or any combination thereof. The I/O 230 may also display images generated based on imaging data.

The communication port 240 may be connected to a network (e.g., the network 120) to facilitate data communications. The communication port 240 may establish connections between the processing device 140 and the scanner 110, the terminal device 130, the storage device 150, or any other component of the imaging system 100. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
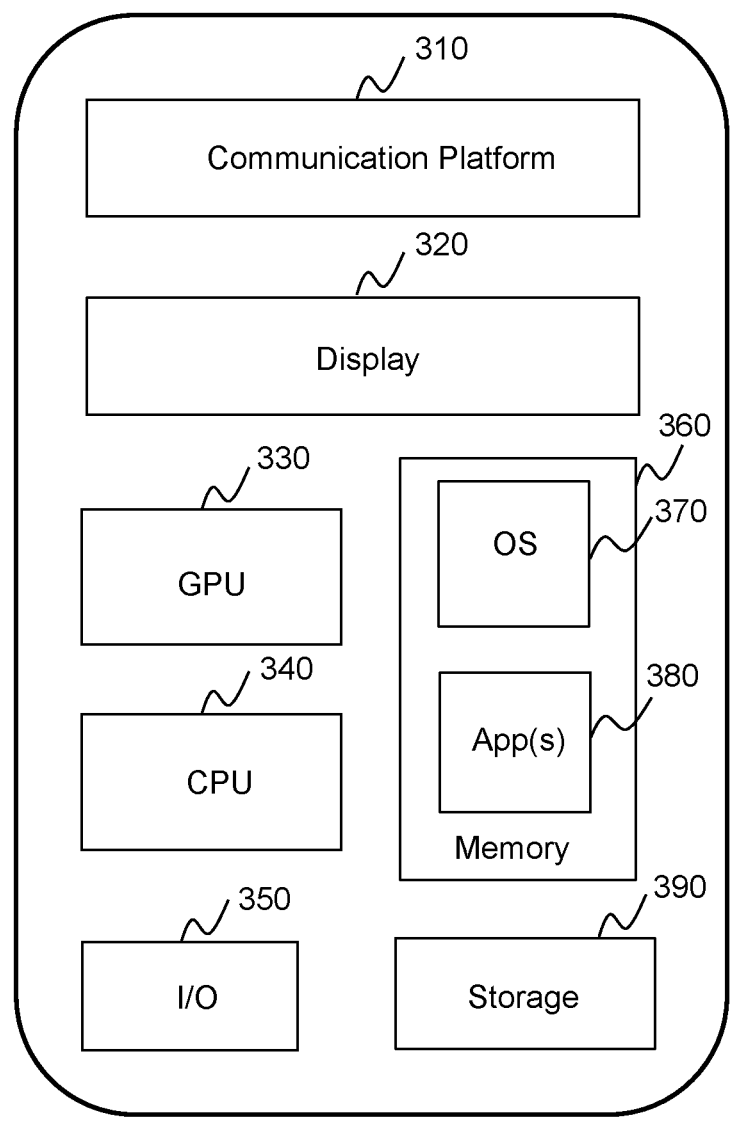
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, the terminal device 130 may be implemented on the mobile device 300. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300.

In some embodiments, a mobile operating system 370 (e.g., iOS, Android, Windows Phone) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 4:
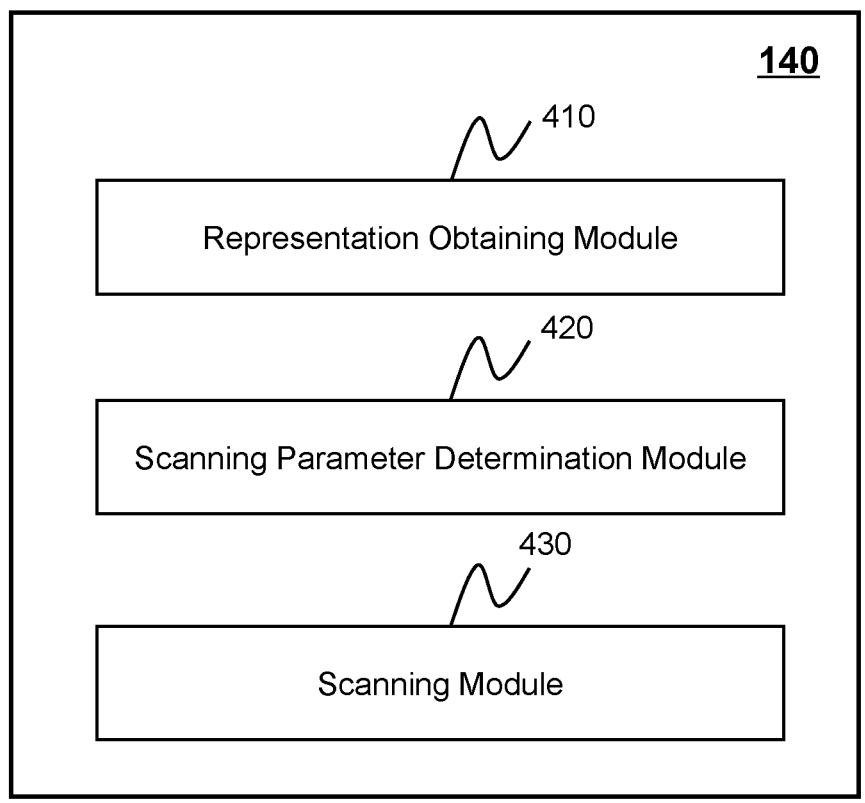
FIG. 4 is a block diagram illustrating an exemplary processing device according to some embodiments of the present disclosure.

FIG. 4 is a block diagram illustrating an exemplary processing device according to some embodiments of the present disclosure. The processing device 140 may include a representation obtaining module 410, a scanning parameter determination module 420, a scanning module 430.

The representation obtaining module 410 may be configured to obtain a representation of a subject. In some embodiments, the representation of the subject may be associated with a real-time image of the subject captured when the subject is on a scanning table and a scan is intended to be performed on the subject. In some embodiments, the representation of the subject may also include a deformable mesh representation of the subject, a kinematical model of the subject, an internal anatomical representation of the subject, or the like, or a combination thereof. Accordingly, the representation obtaining module 410 may be also configured to determine the deformable mesh representation of the subject, the kinematical model of the subject, and/or the internal anatomical representation of the subject based on the real-time image of the subject. In some embodiments, the representation of the subject may also include basic information of the subject. Accordingly, the representation obtaining module 410 may be also configured to obtain the basic information of the subject from a measurement device, from a user input, from a storage device), etc.

The scanning parameter determination module 420 may be configured to determine at least one scanning parameter associated with the subject by automatically processing the representation according to a parameter obtaining model. In some embodiments, the parameter obtaining model may be pre-established based on a plurality of samples associated with a plurality of sample subjects. In some embodiments, the parameter obtaining model may include a machine learning model trained based on the plurality of samples or a library including a plurality of mappings each of which may be between a sample representation and a sample scanning parameter group.

In some embodiments, the scanning parameter determination module 420 may input the representation of the subject into the trained machine learning model and determine an output of the model as the at least one scanning parameter associated with the subject. In some embodiments, the scanning parameter determination module 420 may identify a target sample representation based on a degree of similarity between the first target sample representation and the representation of the subject from the library. Further, the scanning parameter determination module 420 may determine the at least one scanning parameter associated with the subject based on at least one sample scanning parameter included in a sample scanning parameter group corresponding to the target sample representation.

The scanning module 430 may be configured to perform a scan on the subject based at least in part on the at least one scanning parameter. In some embodiments, the scanning module 430 may be configured to perform the scanning on the subject based on the at least one scanning parameter fully automatically. In some embodiments, the scanning module 430 may be configured to perform the scanning on the subject based on the at least one scanning parameter semi-automatically. For example, the scanning module 430 may transmit the at least one scanning parameter associated with the subject to a user, receive from the user an instruction regarding the at least one scanning parameter associated with the subject, and perform the scanning on the subject based at least in part on the at least one scanning parameter and the instruction from the user.

In some embodiments, the processing device 140 may also include a model establishment module (not shown) configured to establish the parameter obtaining model. The model establishment module may obtain a plurality of samples associated with a plurality of sample subjects and establish the parameter obtaining model based on the plurality of samples. In some embodiments, each of the plurality of samples may include a sample representation of a sample subject and a sample scanning parameter group including at least one sample scanning parameter associated with the sample subject. More descriptions regarding establishing the parameter obtaining model may be found elsewhere in the present disclosure (e.g., FIG. 5-B and the description thereof).

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units. For example, the processing device 140 may include a storage module (not shown) used to store information and/or data (e.g., the representation of the subject, the parameter obtaining model, the at least one scanning parameter) associated with the subject. As another example, the processing device 140 (or the scanning module 430) may include a communication module used to transmit the at least one scanning parameter associated with the subject to a user. As a further example, the model establishment module may be unnecessary and the parameter obtaining model may be obtained from a storage device (e.g., the storage device 150) disclosed elsewhere in the present disclosure or may be determined by an independent model establishment device in the imaging system 100 or an external model establishment device.

FIG. 5-A is a flowchart illustrating an exemplary process for imaging according to some embodiments of the present disclosure. In some embodiments, at least part of process 501 may be performed by the processing device 140 (implemented in, for example, the computing device 200 shown in FIG. 2). For example, the process 501 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, one or more modules illustrated in FIG. 4). The operations of the illustrated process presented below are intended to be illustrative. In some embodiments, the process 501 may be accomplished with one or more additional operations not described, and/or without one or more of the operations discussed. Additionally, the order in which the operations of the process 501 as illustrated in FIG. 5-A and described below is not intended to be limiting.

In 510, the processing device 140 (e.g., the representation obtaining module 410) may obtain a representation (e.g., a real-time representation) of a subject. As used herein, the representation of the subject may be any expression form (e.g., an image, a model, a parameter, a mathematical expression (e.g., a value, a vector, a matrix, a formula)) indicating a posture of the subject. Further, a "real-time representation" refers to a representation determined when the subject is on (e.g., lying on) a scanning table or otherwise positioned ready for a scan to be performed on the subject.

In some embodiments, the representation of the subject may be associated with (or include) a real-time image of the subject. As used herein, a "real-time image" refers to an image captured when the subject is on (e.g., lying on) a scanning table or otherwise positioned ready for a scan to be performed on the subject. In some embodiments, the real-time image may include a two-dimensional (2D) image, a three-dimensional (3D) image, a four-dimensional (4D) image, or the like, or any combination thereof. In some embodiments, as described in connection with FIG. 1, the real-time image may be captured by a camera, a sensor (e.g., an optical sensor), a scanner (e.g., a 3D body scanner, a perspective body scanner), etc.

In some embodiments, the representation of the subject may also include a model (e.g., a 2D model, a 3D model) indicating a real-time posture of the subject. For example, the model may include a deformable mesh representation of the subject, a kinematical model of the subject, or the like, or a combination thereof. As used herein, the deformable mesh representation of the subject may refer to a model indicating a body shape (e.g., a 2D body shape, a 3D body shape) of the subject, which may be established based on a set of deformable contours (which can be defined as spline functions) associated with image features (e.g., edges, lines). The kinematical model of the subject may refer to a model indicating a motion of the subject, which includes a set of rigid links connected with joints.

In some embodiments, the representation of the subject may also include an internal anatomical representation of the subject. The internal anatomical representation of the subject may be a representation indicating an internal structure of the subject.

In some embodiments, the processing device 140 may determine the representation in the form of, for example, a deformable mesh representation of the subject, the kinematical model of the subject, and/or the internal anatomical representation of the subject, based on the real-time image of the subject. For example, the processing device 140 may establish a deformable mesh model with one or more adjustable parameters according to a mathematical modeling algorithm. Further, the processing device 140 may extract image features from the real-time image of the subject, input the image features into the deformable mesh model, and determine the deformable mesh representation of the subject based on the image features. As another example, the processing device 140 may establish an original kinematical model with one or more adjustable parameters according to a mathematical modeling algorithm. Further, the processing device 140 may extract image features from the real-time image of the subject, input the image features into the original kinematical model, and determine the kinematical model of the subject based on the image features. As a further example, the processing device 140 may extract one or more anatomical features from the real-time image of the subject and determine the internal anatomical representation (e.g., an anatomical schematic diagram, shapes of organs or tissues, sizes of organs or tissues) of the subject based on the one or more anatomical features.

In some embodiments, the representation of the subject may also include basic information of the subject, for example, a height of the subject, a weight of the subject, a size of the subject, an appearance (e.g., a body type) of the subject, a geometry (e.g., a 2D projection geometry, a 3D geometry) associated with the subject, or the like, or any combination thereof. In some embodiments, the processing device 140 may obtain the basic information of the subject from a measurement device (e.g., a height measurement device, a weighing scale, an infrared scanner, a 3D body scanner) in communication with the imaging system 100. In some embodiments, the processing device 140 may obtain the basic information of the subject from a user input via a user interface (e.g., a user interface of the terminal device 130, a user interface of the processing device 140). In some embodiments, the processing device 140 may obtain the basic information of the subject from a storage device (e.g., the storage device 150, an external data resource) disclosed elsewhere in the present disclosure. For example, the processing device 140 may obtain the basic information of the subject from medical history information of the subject stored in the storage device.

In 520, the processing device 140 (e.g., the scanning parameter determination module 420) may determine at least one scanning parameter associated with the subject by automatically processing the representation according to a parameter obtaining model.

In some embodiments, the at least one scanning parameter may include a scanning range, a scanning dose, a scanning path, a scanning distance, a scanning angle, a scanning sequence, or the like, or a combination thereof. As used herein, the scanning range refers to a region (e.g., a coverage area of the radiation beams) to be scanned on the subject. The scanning dose refers to a dose level of radiation beams emitted from the scanning source (e.g., the X-ray tube in the CT scanner 112, the scanning source in the X-ray scanner 113) of the scanner 110. The scanning path refers to a path along which the radiation beams may pass. The scanning distance refers to a distance between the scanning source and the subject (e.g., a scanning region of the subject). The scanning angle refers to an angle between the scanning path and the horizontal direction or the vertical direction. The scanning sequence refers to a sequence (e.g., a spin echo sequence, a gradient echo sequence, a diffusion sequence, an inversion recovery sequence) used in magnetic resonance imaging.

During the scanning, it may be desired that the scanning range is large enough to cover a target region (e.g., a certain organ, a lesion region on a certain organ) of the subject such that needed information associated with the target region can be obtained. However, if the scanning range is much larger than the target region, it may cause undesired radiation damage to the subject by subjecting regions outside the target region to radiation. Therefore, it is desired that a reasonable scanning range is determined—covering the target region but not much larger than the target region. According to some embodiments of the present disclosure, the processing device 140 may determine the scanning range based on the representation (which indicates, among other things, a posture of the subject) of the subject. According to the representation of the subject, the processing device 140 can identify the target region efficiently and accurately and then determine a suitable scanning range.

In some embodiments, the parameter obtaining model may be pre-established based on a plurality of samples associated with a plurality of sample subjects, wherein each of the plurality of samples may include a sample representation of a sample subject and a sample scanning parameter group including at least one sample scanning parameter associated with the sample subject. As described above, the sample scanning parameter group may include a sample scanning dose, a sample scanning path, a sample scanning distance, a sample scanning angle, a sample scanning range, a sample scanning sequence, or the like, or any combination thereof. More descriptions regarding establishing the parameter extraction mode may be found elsewhere in the present disclosure (e.g., FIG. 5-B and the description thereof).

In some embodiments, the parameter obtaining model may include a machine learning model trained based on the plurality of samples. Accordingly, the processing device 140 may input the representation of the subject into the trained machine learning model and determine an output of the model as the at least one scanning parameter associated with the subject.

In some embodiments, the parameter obtaining model may include a library including a plurality of mappings, wherein each mapping may be between a sample representation and a sample scanning parameter group. Accordingly, the processing device 140 may identify a target sample representation based on a degree of similarity between the target sample representation and the representation of the subject from the library. Then the processing device 140 may determine the at least one scanning parameter associated with the subject based on at least one sample scanning parameter included in a sample scanning parameter group corresponding to the target sample representation. More descriptions regarding determining the at least one scanning parameter associated with the subject may be found elsewhere in the present disclosure (e.g., FIG. 7 and the description thereof).

In 530, the processing device 140 (e.g., the scanning module 430) may perform a scan on the subject based at least in part on the at least one scanning parameter.

In some embodiments, the processing device 140 may perform the scanning on the subject based on the at least one scanning parameter fully automatically. For example, the processing device 140 may determine whether all needed scanning parameters are obtained from the library and/or based on the machine learning model. In response to a determination that the all needed scanning parameters are obtained, the processing device 140 may perform the scanning on the subject fully automatically.

In some embodiments, the processing device 140 may perform the scanning on the subject based on the at least one scanning parameter semi-automatically. For example, in response to a determination that not all needed scanning parameters are obtained, the processing device 140 may provide a notification via a user interface to notify a user to manually set missing scanning parameters. As another example, the processing device 140 may transmit the at least one scanning parameter associated with the subject to the user and receive an instruction (e.g., an approval, a modification, a rejection, a supplement) regarding the at least one scanning parameter associated with the subject from the user. Further, the processing device 140 may perform the scanning on the subject based on the at least one scanning parameter and the instruction from the user. More descriptions regarding performing the scan on the subject may be found elsewhere in the present disclosure (e.g., FIG. 8 and the description thereof).

It should be noted that the above description of the process 501 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the representation of the subject may only include the real-time image of the subject, accordingly, the basic information (e.g., the height of the subject, the weight of the subject, the size of the subject, the appearance of the subject, the geometry of the subject) of the subject, the deformable mesh representation of the subject, the kinematical model of the subject, and/or the internal anatomical representation of the subject may be part of the scanning parameter, which may be determined based on the real-time image of the subject. As another example, one or more other optional operations (e.g., a storing operation) may be added elsewhere in the process 501. In the storing operation, the processing device 140 may store information and/or data (e.g., the representation of the subject, the parameter obtaining model, the at least one scanning parameter) associated with the subject in a storage device (e.g., the storage device 150) disclosed elsewhere in the present disclosure.

FIG. 5-B is a flowchart illustrating an exemplary process for establishing a parameter obtaining model according to some embodiments of the present disclosure. In some embodiments, at least part of process 502 may be performed by the processing device 140 (implemented in, for example, the computing device 200 shown in FIG. 2). For example, the process 502 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, one or more modules illustrated in FIG. 4). The operations of the illustrated process presented below are intended to be illustrative. In some embodiments, the process 502 may be accomplished with one or more additional operations not described, and/or without one or more of the operations discussed. Additionally, the order in which the operations of the process 502 as illustrated in FIG. 5-B and described below is not intended to be limiting.

In 570, the processing device 140 (e.g., a model establishment module in the processing device 140) or a model establishment device may obtain a plurality of samples associated with a plurality of sample subjects, wherein each of the plurality of samples may include a sample representation of a sample subject and a sample scanning parameter group including at least one sample scanning parameter associated with the sample subject. As described in connection with operation 510, the sample scanning parameter group may include a sample scanning dose, a sample scanning path, a sample scanning distance, a sample scanning angle, a sample scanning range, a sample scanning sequence, or the like, or any combination thereof.

In some embodiments, some of the plurality of samples may be obtained by performing a scan on a corresponding sample subject. For example, the processing device 140 may obtain historical scanning parameters in a historical scanning operation performed on a corresponding subject (referred to as "historical subject" for brevity). The processing device 140 may also determine a representation of the historical subject. Further, the processing device 140 may determine the representation of the historical subject and the historical scanning parameters as a sample.

In some embodiments, some of the plurality of samples may be obtained based on a simulation approach. As used herein, the simulation approach may refer to an approach under which simulated scanning parameters (also referred to as "virtual scanning parameters") can be obtained through mathematical computation, rather than an approach under which actual scanning parameters (e.g., historical scanning parameters) can be obtained from actual scanning operations (e.g., historical scanning operations). For example, the processing device 140 may define a sample representation of a sample subject and determine simulated scanning parameters corresponding to the sample representation based on a predetermined algorithm. Further, the processing device 140 may determine the sample representation and the simulated scanning parameters as a sample. In some embodiments, the predetermined algorithm may include an empirical algorithm (e.g., best practice), an algorithm based on a closed form solution (which solves a given problem in terms of functions and mathematical operations from a given generally-accepted set), a nearest neighbor search algorithm (which refers to a form of proximity search for finding a point in a given set that is closest (or most similar) to a given point), or the like, or any combination thereof.

For example, according to the empirical algorithm, for developing organs and/or tissues, the processing device 140 may determine a relatively low scanning dose to reduce radiation effect. As another example, the processing device 140 may establish an equation used for determining scanning distance based on historical scanning parameters according to the closed form solution and determine the scanning distance based on the equation. As a further example, for a specific sample representation, the processing device 140 may determine a historical representation that is closest (or the most similar) to the sample representation by performing a nearest neighbor search on a historical representation set and further determine historical scanning parameters corresponding to the determined historical representation as the simulated scanning parameters. Alternatively or additionally, the processing device 140 may perform the nearest neighbor search on a manifold hyperplane (which refers to a subspace whose dimension is one less than that of its ambient space) of the historical representation set, which can improve search efficiency.

In some embodiments, the processing device 140 may obtain the simulated scanning parameters according to a machine learning algorithm. For example, the processing device 140 may obtain historical representations and historical scanning parameter groups (each of which includes at least one historical scanning parameter) corresponding to the historical representations as a training sample set for training a machine learning model. Each sample in the training sample set includes a historical representation and a historical scanning parameter group (which is used as a label). Then the processing device 140 may determine a preliminary model including one or more preliminary model parameters. For each sample in the training sample set, the processing device 140 may determine a preliminary scanning parameter group based on the preliminary model. Further, the processing device 140 may iteratively update the one or more preliminary model parameters of the preliminary model (e.g., perform an iteration of a backpropagation neural network training procedure (e.g., a stochastic gradient descent backpropagation training technique)) until a plurality of preliminary (or updated) scanning parameter groups corresponding to the samples in the training sample set satisfy a preset condition, for example, the value of a loss function is less than a loss threshold, a difference between the value of the loss function in a previous iteration and the value of the loss function in a current iteration is less than predetermined threshold, a count of iterations (or referred to as an iteration count) is larger than a count threshold, an accuracy rate (which may be determined based on the updated scanning parameter groups and the labels corresponding to the samples, for example, based on a global similarity between the updated scanning parameter groups and the labels) reaches a steady state, etc. Further, the trained machine learning model may be stored in a memory or a storage device (e.g., the storage device 150) disclosed elsewhere in the present disclosure. Accordingly, the processing device 140 may access the trained machine learning model and determine simulated scanning parameters based on a defined sample representation according to the trained machine learning model.

In 580, the processing device 140 (e.g., the model establishment module) or the model establishment device may establish the parameter obtaining model based on the plurality of samples.

In some embodiments, the parameter obtaining model may include a machine learning model trained based on the plurality of samples (for each sample, the corresponding sample scanning parameter group can be used as a label). For example, the processing device 140 may determine a preliminary model including one or more preliminary model parameters. For each of the plurality of samples, the processing device 140 may determine a preliminary scanning parameter group based on the preliminary model. Further, the processing device 140 may iteratively update the one or more preliminary model parameters of the preliminary model (e.g., perform an iteration of a backpropagation neural network training procedure (e.g., a stochastic gradient descent backpropagation training technique)) until a plurality of preliminary (or updated) scanning parameter groups corresponding to the plurality of samples satisfy a preset condition, for example, a loss function is less than a loss threshold, a difference between the value of the loss function in a previous iteration and the value of the loss function in a current iteration is less than predetermined threshold, a count of iterations is larger than a count threshold, an accuracy rate (which may be determined based on the updated scanning parameter groups and the labels corresponding to the samples, for example, based on a global similarity between the updated scanning parameter groups and the labels) reaches a steady state, etc. Further, the trained machine learning model may be stored in a memory or a storage device (e.g., the storage device 150) disclosed elsewhere in the present disclosure.

In some embodiments, the parameter obtaining model may include a library including a plurality of mappings, wherein each mapping may be between a sample representation and a sample scanning parameter group. In some embodiments, the processing device 140 may establish the library in the form of a table, a graph, a tree structure, etc. More descriptions of the library may be found elsewhere in the present disclosure (e.g., FIG. 6 and the description thereof).

It should be noted that the above description of the process 501 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the process 502 may be performed by an independent model establishment device in the imaging system 100 or by an external model establishment device. As another example, the plurality of samples may be obtained from the storage device 150 or an external data resource. As a further example, the process 502 may be performed online or offline.

FIG. 6-A and FIG. 6-B are schematic diagrams illustrating exemplary mappings between sample representations and sample scanning parameter groups according to some embodiments of the present disclosure.

As described in connection with FIG. 5-B, the library may include a plurality of mappings each of which is between a sample representation and a sample scanning parameter group. As illustrated in FIG. 6-A, the library includes a data set $X_1$ storing the sample representations (e.g., a, b, c) and a data set $X_2$ storing the sample scanning parameter groups (e.g., A, B, C). The mappings between the sample representations and the sample scanning parameter groups may be realized via pointers between the two data sets. As illustrated in FIG. 6-B, the sample representations and the sample scanning parameter groups may be stored in the library in a form of a data table including a first column indicating "sample representation" and a second column indicating "sample scanning parameter group."

Figure 7:
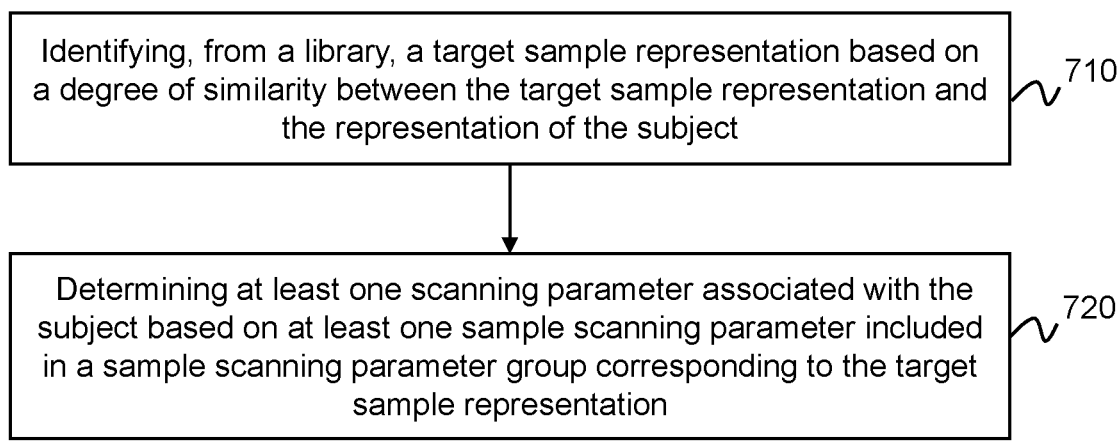
FIG. 7 is a flowchart illustrating an exemplary process for determining at least one scanning parameter associated with a subject according to some embodiments of the present disclosure.

FIG. 7 is a flowchart illustrating an exemplary process for determining at least one scanning parameter associated with a subject according to some embodiments of the present disclosure. In some embodiments, at least part of process 700 may be performed by the processing device 140 (implemented in, for example, the computing device 200 shown in FIG. 2). For example, the process 700 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, one or more modules illustrated in FIG. 4). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 710, the processing device 140 (e.g., the scanning parameter determination module 420) may identify a target sample representation (also referred to as "first target sample representation") based on a degree of similarity (also referred to as "first degree of similarity") between the target sample representation and the representation of the subject in the library.

As described in connection with FIG. 5-B, the library is pre-established based on the plurality of samples and includes a plurality of mappings each of which is between a sample representation and a sample scanning parameter group. In some embodiments, for each of at least some of the plurality of mappings, the processing device 140 may determine a degree of similarity between a sample representation of the mapping and the representation of the subject. As used herein, the similarity may include a mean distance similarity (e.g., a mean Euclidean distance similarity, a mean Hamming distance similarity, a mean Manhattan distance similarity, a mean Minkowski distance similarity), a cosine similarity, a normalized cross-correlation, mutual information, a correlation ratio, a Jaccard similarity, a Pearson correlation, an overlap coefficient, or the like, or any combination thereof. Further, the processing device 140 may identify a sample representation corresponding to a mapping of the at least some mappings as the target sample representation based on the determined degrees of similarities.

In some embodiments, the processing device 140 may determine a vector corresponding to the representation of the subject and a sample vector corresponding to the sample representation, and further determine the degree of similarity between the representation of the subject and the sample representation based on the two vectors.

In some embodiments, the processing device 140 may determine the degree of similarity based on a machine learning model (e.g., a recurrent neural network (RNN) model, a convolutional neural network (CNN) model). For example, the processing device 140 may obtain sample representations (e.g., historical representations, simulated representations) as a training sample set for training a machine learning model. Each sample in the training sample set includes a pair of sample representations with a label (e.g., "0," "1") indicating a similarity between the pair of sample representations. Then the processing device 140 may determine a preliminary model including one or more preliminary model parameters. For each sample (i.e., a pair of sample representations) in the training sample set, the processing device 140 may determine a preliminary similarity based on the preliminary model. Further, the processing device 140 may iteratively update one or more preliminary model parameters of the preliminary model (e.g., perform an iteration of a backpropagation neural network training procedure (e.g., a stochastic gradient descent backpropagation training technique)) until a plurality of preliminary (or updated) similarities corresponding to the samples in the training sample set satisfy a preset condition, for example, a loss function is less than a loss threshold, a difference between the value of the loss function in a previous iteration and the value of the loss function in a current iteration is less than predetermined threshold, a count of iterations is larger than a count threshold, an accuracy rate (which may be determined based on the updated similarities and the labels corresponding to the samples, for example, based on a global similarity between the updated similarities and the labels) reaches a steady state, etc. Further, the trained machine learning model may be stored in a memory or a storage device (e.g., the storage device 150) disclosed elsewhere in the present disclosure. Accordingly, the processing device 140 may access the trained machine learning model and determine the degree of similarity between the sample representation of the mapping and the representation of the subject according to the trained machine learning model.

In some embodiments, the processing device 140 may identify the highest degree of similarity among the degrees of similarities corresponding to the at least some mappings. Further, the processing device 140 may designate a sample representation corresponding to the highest degree of similarity as the target sample representation.

In some embodiments, the processing device 140 may designate a sample representation corresponding to a mapping of the at least some mappings whose degree of similarity with the representation of the subject is higher than a threshold as the target sample representation. In some embodiments, the threshold may be a default setting of the imaging system 100 or may be adjustable under different situations. In some embodiments, there may be two or more sample representations whose degrees of similarities with the representation of the subject are higher than the threshold. In this situation, the processing device 140 may randomly select a sample representation from the two or more sample representations as the target sample representation.

In 720, the processing device 140 (e.g., the scanning parameter determination module 420) may determine at least one scanning parameter associated with the subject based on at least one sample scanning parameter included in a sample scanning parameter group corresponding to the target sample representation.

In some embodiments, the processing device 140 may designate the at least one sample scanning parameter included in the sample scanning parameter group corresponding to the target sample representation as the at least one scanning parameter associated with the subject.

In some embodiments, the processing device 140 may determine whether the at least one sample scanning parameter included in the sample scanning parameter group corresponding to the target sample representation satisfies a predetermined condition. For example, the processing device 140 may perform a pre-scanning or a simulated scanning based on the at least one sample scanning parameter, obtain a pre-scanning result or a simulated scanning result (e.g., an image), and further analyze the pre-scanning result or the simulated scanning result. In response to determining that a coverage range of a target organ in the image is less than a predetermined range threshold or the target organ is not completely included in the image, the processing device 140 may determine that the at least one sample scanning parameter included in the sample scanning parameter group corresponding to the target sample representation does not satisfy the predetermined condition.

In some embodiments, in response to determining that the at least one sample scanning parameter does not satisfy the predetermined condition, the processing device 140 may determine the at least one scanning parameter associated with the subject by modifying the at least one sample scanning parameter included in the sample scanning parameter group corresponding to the target sample representation. For example, in response to determining that the target organ is not completely included in the image, the processing device 140 may expand the scanning range.

In some embodiments, in response to determining that the at least one sample scanning parameter does not satisfy the predetermined condition, the processing device 140 may identify a second target sample representation based on a second degree of similarity between the second target sample representation and the representation of the subject from the library. For example, the processing device 140 may identify the second highest degree of similarity (relative to the highest degree of similarity) among the degrees of similarities corresponding to the at least some mappings and designate a sample representation corresponding to the second highest degree of similarity as the second target sample representation. As another example, as described above, there may be two or more sample representations whose degrees of similarities with the representation of the subject are higher than a threshold. The processing device 140 may randomly select another sample representation from the two or more sample representations as the second target sample representation.

Further, the processing device 140 may determine the at least one scanning parameter associated with the subject based on at least one sample scanning parameter included in a sample scanning parameter group corresponding to the second target sample representation. Similar to above, for example, the processing device 140 may designate the at least one sample scanning parameter included in the sample scanning parameter group corresponding to the second target sample representation as the at least one scanning parameter associated with the subject. As another example, the processing device 140 may determine whether the at least one sample scanning parameter included in the sample scanning parameter group corresponding to the second target sample representation satisfies a predetermined condition. In response to a determination that the at least one sample scanning parameter does not satisfy the predetermined condition, the processing device 140 may determine the at least one scanning parameter associated with the subject by modifying the at least one sample scanning parameter included in the sample scanning parameter group corresponding to the second target sample representation or further identify a third target sample representation based on a third degree of similarity between the third target sample representation and the representation of the subject until the determined at least one sample scanning parameter satisfies the predetermined condition.

It should be noted that the above description of the process 700 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, if there is no target representation is identified from the library (e.g., all the degrees of similarities between the sample representations in the library and the representation of the subject are less than or equal to the threshold), the at least on scanning parameter associated with the subject may be determined manually or automatically (e.g., according to the predetermined algorithm for determining the simulated scanning parameters described in FIG. 5-B). Further, a mapping between the representation of the subject and the at least one scanning parameter may be added into the library for further use.

Figure 8:
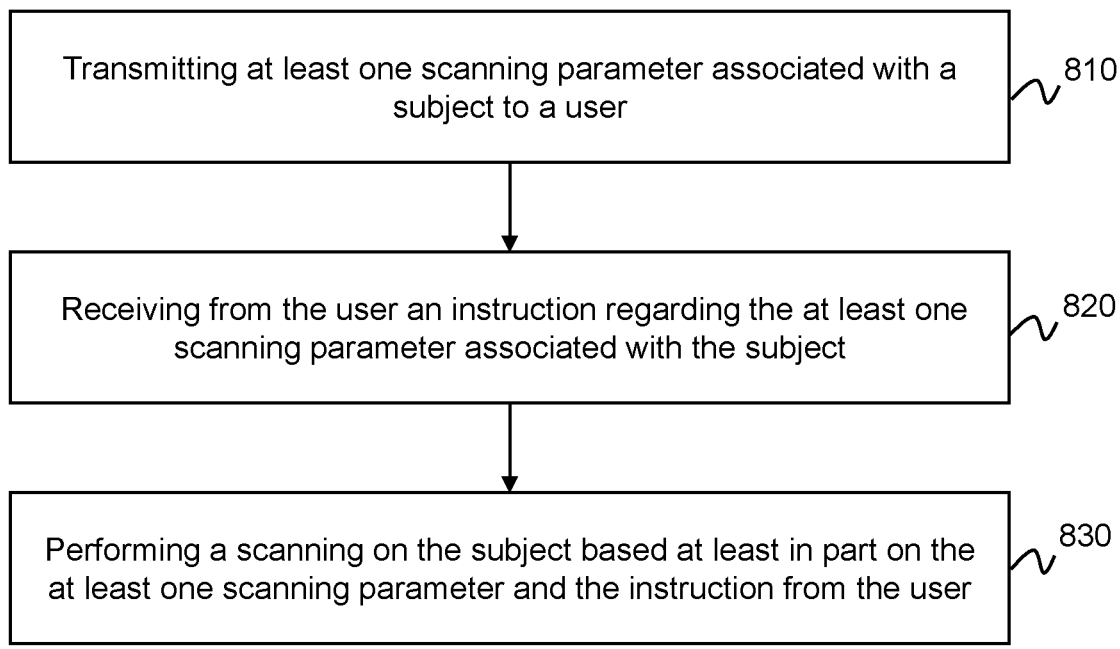
FIG. 8 is a flowchart illustrating an exemplary process for performing a scan on a subject based at least in part on at least one scanning parameter according to some embodiments of the present disclosure.

FIG. 8 is a flowchart illustrating an exemplary process for performing a scan on a subject based at least in part on at least one scanning parameter according to some embodiments of the present disclosure. In some embodiments, at least part of process 800 may be performed by the processing device 140 (implemented in, for example, the computing device 200 shown in FIG. 2). For example, the process 800 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, one or more modules illustrated in FIG. 4). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In 810, the processing device 140 (e.g., the scanning module 430) may transmit the at least one scanning parameter associated with the subject to a user (e.g., a doctor, an operator, a technician).

In some embodiments, the processing device 140 may transmit the at least one scanning parameter associated with the subject to the terminal device 130 via the communication port 240. The communication port 240 may establish a connection (e.g., a wired connection, a wireless connection) between the processing device 140 and the terminal device 130. Then the terminal device 130 may receive the at least one scanning parameter associated with the subject via the communication platform 310 and further display the at least one scanning parameter via the display 320 or the I/O 350.

In some embodiments, the processing device 140 may transmit the at least one scanning parameter associated with the subject to the I/O 230 via an internal bus in the processing device 140. Then the I/O 230 may display the at least one scanning parameter via an interface.

In 820, the processing device 140 (e.g., the scanning module 430) may receive from the user an instruction regarding the at least one scanning parameter associated with the subject. In some embodiments, the user may input the instruction via the I/O 230 or the I/O 350.

In some embodiments, the instruction may include an approval to designate the at least one scanning parameter associated with the subject as a scanning parameter for the scanning, a modification of at least a portion of the at least one scanning parameter associated with the subject, a rejection of at least a portion of the at least one scanning parameter associated with the subject, a supplement to the at least one scanning parameter associated with the subject, or the like, or a combination thereof. The user may determine whether the at least one scanning parameter associated with the subject satisfies imaging needs (based on, for example, intended use of the image so acquired) or clinical standards and determine an approval, a modification, a rejection, and/or a supplement associated with the at least one scanning parameter.

In 830, the processing device 140 (e.g., the scanning module 430) may perform the scanning on the subject based at least in part on the at least one scanning parameter and the instruction from the user.

In some embodiments, if the instruction from the user is the approval to designate the at least one scanning parameter associated with the subject as the scanning parameter for the scanning, the processing device 140 may perform the scanning on the subject based on the at least one scanning parameter directly.

In some embodiments, if the instruction from the user is the modification of at least a portion of the at least one scanning parameter associated with the subject, the processing device 140 may modify the portion of the at least one scanning parameter associated with the subject based on the instruction and perform the scanning on the subject based at least in part on the modified at least one scanning parameter associated with the subject.

In some embodiments, if the instruction is the rejection of at least a portion of the at least one scanning parameter associated with the subject, the processing device 140 may delete the portion of the at least one scanning parameter and perform the scanning on the subject based on remainder scanning parameter(s) and/or one or more manually set scanning parameters.

In some embodiments, if the instruction is the supplement to the at least one scanning parameter associated with the subject, the processing device 140 may supplement at least one additional scanning parameter to the at least one scanning parameter associated with the subject based on the instruction and perform the scanning on the subject based at least in part on the supplemented at least one scanning parameter associated with the subject including the at least one additional scanning parameter.

It should be noted that the above description of the process 800 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this disclosure are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction performing system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A system for imaging, comprising:
at least one storage medium including a set of instructions; and
at least one processor in communication with the at least one storage medium, wherein when executing the set of instructions, the at least one processor is directed to cause the system to perform operations including:
obtaining a real-time representation of a subject;
determining at least one scanning parameter associated with the subject by automatically processing the representation according to a parameter obtaining model, wherein the parameter obtaining model includes a library including a plurality of mappings, each mapping being between a sample representation of a sample subject and a sample scanning parameter group including at least one sample scanning parameter associated with the sample subject, and the determining the at least one scanning parameter associated with the subject by automatically processing the representation according to the parameter obtaining model includes:
identifying, from the library, a target sample representation based on a degree of similarity between the target sample representation and the representation of the subject; and
designating at least one sample scanning parameter included in a sample scanning parameter group corresponding to the target sample representation as the at least one scanning parameter associated with the subject; and
performing a scan on the subject based at least in part on the at least one scanning parameter.

2. The system of claim 1, wherein the representation of the subject includes a real-time image of the subject, a model indicating a real-time posture of the subject, or an internal anatomical representation of the subject.

3. The system of claim 1, wherein the at least one scanning parameter includes at least one of a scanning range, a scanning dose, a scanning path, a scanning distance, a scanning angle, or a scanning sequence.

4. The system of claim 1, wherein
the parameter obtaining model is pre-established based on a plurality of samples associated with a plurality of sample subjects; and
each of the plurality of samples includes a sample representation and a corresponding sample scanning parameter group.

5. The system of claim 4, wherein each of the plurality of samples is obtained by performing a scan on a sample subject or a simulation approach.

6. The system of claim 4, wherein the parameter obtaining model includes a machine learning model trained based on the plurality of samples.

7. The system of claim 1, wherein the identifying, from the library, the target sample representation based on the degree of similarity between the target sample representation and the representation of the subject includes:
for each of at least some of the plurality of mappings,
determining a degree of similarity between a sample representation of the mapping and the representation of the subject; and
identifying, based on the determined degrees of similarities, a sample representation corresponding to a mapping of the at least some mappings as the target sample representation.

8. The system of claim 7, wherein the degree of similarity between a sample representation of the mapping and the representation of the subject is determined based on a machine learning model.

9. The system of claim 7, wherein the identifying, based on the determined degrees of similarities, the sample representation corresponding to the mapping of the at least some mappings as the target sample representation includes:
designating a sample representation corresponding to a mapping of the at least some mappings whose degree of similarity with the representation of the subject is higher than a threshold as the target sample representation.

10. The system of claim 1, wherein the determining the at least one scanning parameter associated with the subject by automatically processing the representation according to the parameter obtaining model further includes:
determining the at least one scanning parameter associated with the subject by modifying the at least one sample scanning parameter included in the sample scanning parameter group corresponding to the target sample representation.

11. The system of claim 1, wherein the determining the at least one scanning parameter associated with the subject by automatically processing the representation according to the parameter obtaining model further includes:
identifying, from the library, a second target sample representation based on a second degree of similarity between the second target sample representation and the representation of the subject; and
determining the at least one scanning parameter associated with the subject based on at least one sample scanning parameter included in a sample scanning parameter group corresponding to the second target sample representation.

12. The system of claim 1, wherein the at least one processor is directed to cause the system to perform the operations further including:

transmitting the at least one scanning parameter associated with the subject to a user;

receiving from the user an instruction regarding the at least one scanning parameter associated with the subject; and performing the scan on the subject based at least in part on the at least one scanning parameter and the instruction from the user.

13. The system of claim 12, wherein the instruction includes at least one of an approval to designate the at least one scanning parameter associated with the subject as a scanning parameter for the scanning, a modification of at least a portion of the at least one scanning parameter associated with the subject, a rejection of at least a portion of the at least one scanning parameter associated with the subject, or a supplement to the at least one scanning parameter associated with the subject.

14. The system of claim 13, wherein the at least one processor is directed to cause the system to perform the operations further including:

modifying at least a portion of the at least one scanning parameter associated with the subject based on the instruction; and performing the scan on the subject based at least in part on the modified at least one scanning parameter associated with the subject.

15. The system of claim 13, wherein the at least one processor is directed to cause the system to perform the operations further including:

supplementing at least one additional scanning parameter to the at least one scanning parameter associated with the subject based on the instruction; and performing the scan on the subject based at least in part on the supplemented scanning parameter associated with the subject including the at least one additional scanning parameter.

16. A method for imaging, comprising:

obtaining a real-time representation of a subject;

determining at least one scanning parameter associated with the subject by automatically processing the representation according to a parameter obtaining model, wherein the parameter obtaining model includes a library including a plurality of mappings, each mapping being between a sample representation of a sample subject and a sample scanning parameter group including at least one sample scanning parameter associated with the sample subject, and the determining the at least one scanning parameter associated with the subject by automatically processing the representation according to the parameter obtaining model includes:

identifying, from the library, a target sample representation based on a degree of similarity between the target sample representation and the representation of the subject; and designating at least one sample scanning parameter included in a sample scanning parameter group corresponding to the target sample representation as the at least one scanning parameter associated with the subject; and performing a scan on the subject based at least in part on the at least one scanning parameter.

17. The method of claim 16, wherein the representation of the subject includes a real-time image of the subject, a model indicating a real-time posture of the subject, or an internal anatomical representation of the subject.

18. The method of claim 16, wherein the at least one scanning parameter includes at least one of a scanning range, a scanning dose, a scanning path, a scanning distance, a scanning angle, or a scanning sequence.

19. The method of claim 16, further comprising:

transmitting the at least one scanning parameter associated with the subject to a user;

receiving from the user an instruction regarding the at least one scanning parameter associated with the subject; and performing the scan on the subject based at least in part on the at least one scanning parameter and the instruction from the user.

20. A non-transitory computer readable medium, comprising executable instructions that, when executed by at least one processor, direct the at least one processor to perform a method, the method comprising:

obtaining a real-time representation of a subject;

determining at least one scanning parameter associated with the subject by automatically processing the representation according to a parameter obtaining model, wherein the parameter obtaining model includes a library including a plurality of mappings, each mapping being between a sample representation of a sample subject and a sample scanning parameter group including at least one sample scanning parameter associated with the sample subject, and the determining the at least one scanning parameter associated with the subject by automatically processing the representation according to the parameter obtaining model includes:

identifying, from the library, a target sample representation based on a degree of similarity between the target sample representation and the representation of the subject; and designating at least one sample scanning parameter included in a sample scanning parameter group corresponding to the target sample representation as the at least one scanning parameter associated with the subject; and performing a scan on the subject based at least in part on the at least one scanning parameter.

* * * * *